United States Patent [19]

Cesa et al.

[11] Patent Number: 5,324,856
[45] Date of Patent: Jun. 28, 1994

[54] MAKING OPTICALLY ACTIVE ALPHA-HYDROXY ACIDS OR PRECURSORS

[76] Inventors: Mark C. Cesa; Robert A. Dubbert; James D. Burrington, all of 200 Public Sq. 7-A-6666, Cleveland, Ohio 44114

[21] Appl. No.: 930,245

[22] Filed: Aug. 17, 1992

Related U.S. Application Data

[63] Continuation-in-part of Ser. No. 749,495, Aug. 16, 1991, abandoned, which is a continuation of Ser. No. 661,950, Feb. 28, 1991, abandoned, which is a continuation-in-part of Ser. No. 498,668, Mar. 26, 1990, abandoned, which is a continuation-in-part of Ser. No. 792,418, Oct. 29, 1985, abandoned.

[51] Int. Cl.$^5$ .............................................. C07C 59/08
[52] U.S. Cl. .................... 562/589; 560/114; 560/185; 560/233; 562/401; 562/579; 562/581
[58] Field of Search ............... 560/114, 233, 185; 562/589, 579, 581, 401

[56] References Cited

U.S. PATENT DOCUMENTS 4,377,708  3/1983  Morris ................................ 560/266

FOREIGN PATENT DOCUMENTS 144118  6/1985  European Pat. Off. .
418943  11/1934  United Kingdom .

OTHER PUBLICATIONS

Migrdichian, "Organic Synthesis," vol. 1, p. 205 (1957).
March, "Advanced Organic Chemistry, Reactions, Mechanisms and Structure," pp. 92–94 (1969).
March, "Advanced Organic Chemistry, Reactions, Mechanisms and Structure," 2nd Ed., pp. 736–737 (1977).
Roberts, "Basic Principles of Organic Chemistry," pp. 597–603 (1964).

*Primary Examiner*—Michael L. Shippen

[57] ABSTRACT

Disclosed is a process for making an α-hydroxy acid which is essentially all L or all D with respect to the chiral C atom bonded to the carboxy group of said acid which comprises (1) hydrocarboxylating an enol acylate, which has a chiral C atom that is essentially all L or all D, with CO and water or an organic hydroxyl compound, thereby producing a reaction mixture containing diastereomeric α-acyloxy acids or esters having two chiral centers and having essentially no enantiomeric pairs, (2) separating the diastereomers by conventional physical means and (3) hydrolyzing at least one of said separated diastereomers to make at least the α-hydroxy acid which is essentially all L or all D with respect to the chiral C atom bonded to the carboxy group of said acid.

Also disclosed is a process for making an α-hydroxy acid which is essentially all L or all D with respect to the chiral C atom bonded to the carboxy group of said acid which comprises (1) hydrocarboxylating an enol acylate, the enol portion of which has a chiral C atom that is essentially all L or all D, with CO and water or an organic hydroxyl compound, thereby producing a reaction mixture containing diastereomeric α-acyloxy acids or esters having two chiral centers and having essentially no enantiomeric pairs, (2) hydrolyzing the product of (1) to make a diastereomeric mixture containing α-hydroxy acids, and (3) separating by conventional physical means from the product of (2) at least one α-hydroxy acid which is essentially all L or all D with respect to the chiral C atom bonded to the carboxy group of said acid.

8 Claims, No Drawings

MAKING OPTICALLY ACTIVE ALPHA-HYDROXY ACIDS OR PRECURSORS

This application is a continuation-in-part of Ser. No. 749,495, filed Aug. 16, 1991, now abandoned, which is a continuation of Ser. No. 661,950, filed Feb. 28, 1991, now abandoned, which is a continuation-in-part of application Ser. No. 498,668 filed Mar. 26, 1990, now abandoned, which is a continuation-in-part of application Ser. No. 792,418 filed Oct. 29, 1985, now abandoned.

This invention relates to a process for making an optically active mixture of an $\alpha$-acyloxy acid or ester containing at least two chiral centers.

In another aspect this invention relates to a process for making an essentially all L or all D $\alpha$-hydroxy acid without ever having any enantiomeric mixture either (1) of L and D $\alpha$-hydroxy acids or esters or (2) of enantiomeric sterioisomers of L and D $\alpha$-acyloxy acids or esters.

The separation of enantiomers by physical means such as fractional distillation or fractional crystallization and the like is known to be highly difficult in general.

It is an object of the invention to provide a process to produce a reaction mixture containing $\alpha$-acyloxy acids or esters having two (at least) chiral centers, which mixture contains two of four possible optical configurations and contains substantially no enantiomeric pairs.

Another object is to provide a process for making an essentially all L or all D $\alpha$-hydroxy acid without the necessity of separating enantiomers at any stage of the process.

Other objects, as well as features, aspects, and advantages, of the invention will become apparent from a study of the specification, including the examples and the claims.

We have now conceived a process for making an optically active mixture of an $\alpha$-acyloxy acid or ester containing essentially no enantiomeric pairs. Thus, in accordance with the present invention we have provided a process for making an easily separable reaction mixture containing diastereomeric $\alpha$-acyloxy acids or esters having at least two chiral centers, which process comprises hydrocarboxylating an essentially optically pure chiral enol acylate (essentially all D or all L) to produce a reaction mixture containing the diastereomeric $\alpha$-acyloxy acids or esters having two chiral centers. The hydrocarboxylation is effected using water or an organic hydroxyl compound, usually an aliphatic alcohol, and carbon monoxide as the hydrocarboxylation reagents in the reaction with the enol acylate.

In another aspect of the invention there is provided a process for making an essentially all L or all D $\alpha$-hydroxy acid which comprises (1) hydrocarboxylating an enol acylate, which has a chiral C atom that is essentially all L or all D, with CO and water or an organic hydroxyl compound, thereby producing a reaction mixture containing diastereomeric $\alpha$-acyloxy acids or esters having two chiral centers and having essentially no enantiomeric pairs, (2) separating the diastereomers by conventional physical means and (3) hydrolyzing at least one of said separated diastereomers to make at least the L or the D-$\alpha$-hydroxy acid, said hydrocarboxylating step simultaneously creating (a) said $\alpha$-acyloxy acid or ester (b) the chirality of the alpha C atom in L, D form and (c) the second chiral center in said $\alpha$-acyloxy acid or ester in essentially all L or all D form.

When one of the constituents of a carbon atom of the carbon-to-carbon double bond of the enol acylate contains a chiral C atom, the separation of the diastereomers can precede the hydrolysis, as noted in the last paragraph. However, alternatively, these steps can be reversed. Thus, step (2) can be the hydrolysis and step (3) the separation of the diastereomers that still do have two chiral carbon atoms. This procedure can be followed whether or not a constituent bound to the carbonyl C atom of the acyl group contains a chiral carbon atom.

Further in accordance with the present invention, there is provided a process which comprises reacting a chiral enol acylate that is essentially free of enantiomeric pairs according to the equation:

$$R_1R_2C=C(R_3)OCOR_4 + CO + R_5OH \rightarrow R_1R_2CHC(R_3)(OCOR_4)COOR_5$$

to produce an essentially diastereomeric mixture of two $\alpha$-acyloxy acids or esters having at least two chiral carbons, wherein (A) the carbon bonded to $R_3$ in the product is chiral, (B) $R_3$ is not the same as —$CHR_1R_2$, —$COOR_5$, or —$OCOR_4$, (C) each of $R_1$, $R_2$, $R_3$, $R_4$, and $R_5$ contains no ethylenic or acetylenic unsaturation, (D) each of $R_1$, $R_2$, $R_3$, and $R_4$ is independently selected from H and a hydrocarbyl group having 1–15 carbon atoms, and $R_5$ is H or a hydrocarbyl group having 1–15 carbon atoms, which optionally contains one or more hydroxyl groups, (E) $R_1$ and $R_2$, $R_1$ and $R_3$, or $R_2$ and $R_3$ can be linked to form a ring, and (F) at least one of $R_1$, $R_2$, $R_3$, and $R_4$ contains a chiral carbon atom.

If the chiral enol acylate starting material essentially free of enantiomeric pairs is the L isomer, the reaction product mixture contains the diastereomeric $\alpha$-acyloxy acids or esters of the configurations DL and LL, where the first designation is the configuration at the alpha carbon atom and the second is the configuration of the chiral center in $R_1$, $R_2$, $R_3$, or $R_4$ as the case may be. If the starting material is essentially all D optical isomer, the diastereomeric reaction product mixture contains the diastereomeric $\alpha$-acyloxy acids or esters of the configurations DD and LD.

In the foregoing reaction $R_1$, $R_2$, $R_3$, $R_4$ and $R_5$ are usually limited to a maximum of 10 carbon atoms. The most common $R_5OH$ reactant is a saturated monohydric aliphatic alcohol.

The process of the invention for making the mixture containing two (or more) diastereomeric $\alpha$-acyloxy acids or esters is of importance in providing a source for relatively easily obtaining a particular stereoisomeric configuration of a given $\alpha$-hydroxy acid separated from any other stereoisomer thereof. Thus, the mixture made according to the present invention can be resolved by one of two procedures. If the chiral group in the enol acylate is in $R_4$, the two diastereomers are separated physically by well known physical means, such as fractional crystallization, fractional absorption on solid absorbents, countercurrent solvent extraction, fractional distillation where feasible, or other physical means. For a discussion see, for instance, J. Jacques, A. Collet ad S. H. Wiler, *Enantiomers, Racemates, and Resolutions*, New York, 1981, Chapters 5 and 7. Thereafter, the product fractions are separately hydrolyzed in the presence of an acid or base in the conventional manner to obtain the corresponding $\alpha$-hydroxy acids and the chiral, optically active (L or D) carboxylic acid.

This method is especially useful and allows an recycle of the chiral L or D acid in an overall process to be discussed hereafter.

When $R_1$, $R_2$, or $R_3$ contains the chiral C atom and $R_4$ does not, the same procedure as above can be followed. Alternatively, however, the hydrolysis can be effected first and then the DL and LL (or the DD and LD) products separated by such physical means as discussed above.

The present invention is of considerable value in providing a route for making the L form or the D form of hydroxy acids occurring in nature, for example, lactic acid. In this aspect of the invention the product is a diastereomeric mixture containing α-acyloxy acids or esters that are hydrolyzable to naturally occurring α-hydroxy acids. The present invention is of considerable advantage when compared to present methods. Thus, optically pure α-hydroxy acids are produced industrially by the following methods:
 a) fermentation
 b) chemical synthesis using HCN as a one-carbon source, followed by derivatization and resolution and de-derivatization.

Fermentation processes, while they give highly enantiomerically pure product, are costly and insufficient in that they produce large amounts of by-products, making product purification expensive and troublesome. The chemical routes are highly corrosive, consume stoichiometric amounts of toxic and expensive HCN and $H_2SO_4$, produce stoichiometric amounts of low-value ammonium sulfate by-product, and require several extra steps to carry out the enantiomeric resolution.

The advantages of the process of this invention are
 1. cheap high yield chemical synthesis
  -CO to replace HCN
  -no non-recyclable by-products
  -very high conversions and selectivities
 2. Diastereomers are created in the hydrocarboxylation step, eliminating the need for subsequent derivatization steps.
 3. Easy product purification and by-product recycle.

In a particularly advantageous aspect of the present invention there is provided a process which comprises (1) reacting a chiral carboxylic acid halide or anhydride, whose chiral C atom is essentially all L or all D, with an aldehyde or ketone to make an optically active enol acylate that is essentially all L or all D, (2) hydrocarboxylating said enol acylate with CO and water or an organic hydroxyl compound, thereby producing a hydrocarboxylation reaction mixture containing diastereomeric α-acyloxy acids or esters having two chiral centers and having essentially no enantiomeric pairs, (3) separating the diastereomers by conventional physical means, (4) hydrolyzing each diastereomer to make the L and D α-hydroxy acids, respectively, plus said organic acid, and recycling at least a part of said organic acid (after conversion to the halide or anhydride) to step (1).

Alternatively the recycle process comprises (1) reacting a chiral carboxylic acid whose chiral C atom is essentially all L or all D with oxygen and an olefin by the Wacker reaction to make an optically active enol acylate that is essentially all L or all D, (2) hydrocarboxylating said enol acylate with CO and water or an organic hydroxyl compound, thereby producing a hydrocarboxylation reaction mixture containing diastereomeric α-acyloxy acids or esters having two chiral centers and having essentially no enantiomeric pairs, (3) separating the diastereomers by conventional physical means, (4) hydrolyzing each diastereomer to make the L and D α-hydroxy acids, respectively, plus said organic acid, and recycling at least a part of said organic acid to step (1).

European patent application no. 84 305,611.0, published Jun. 12, 1985, under Publication No. 0144,118, discloses the details of how to hydrocarboxylate enol acylates with carbon monoxide and an organic hydroxyl compound. Reference is made to this document for the details of carrying out the hydrocarboxylation, and the disclosures of this European patent application in this regard are incorporated herein by reference.

It should be noted that in such a hydrocarboxylation, the alpha carbon atom in the hydrocarboxylation product is chiral. Therefore, the α-acyloxy acid or ester produced is a racemic mixture of the L and D forms. If one wants either the L form or the D form without its enantiomer, the separation is difficult and expensive.

The crux of the broadest aspect of the present invention is the concept of employing an enol acylate starting material in the foregoing reaction that is essentially all L or all D so that when the reaction is carried out, the product will contain essentially no enantiomeric pairs, as previously discussed. Since the product mixture has no enantiomeric pairs, the stereoisomers can be more easily separated by physical means than can a reaction mixture containing enantiomeric pairs.

The hydrocarboxylation reaction is carried out catalytically, discussed in more detail hereafter. It can be carried out continuously or in a batch operation in the liquid or vapor phase. Usually the reaction is carried out in a batch operation in a solvent under pressure.

The reactant concentrations can vary widely and are not in general critical. The ratio of hydroxyl reactant to the enol acylate is usually no greater than 10/1 on a molar basis. However, when $R_4$ has the chiral (essentially all L or all D) C atom, this ratio should be low enough so that part of the hydrocarboxylation product is not an α-hydroxy acid or ester because of transesterification. Generally, the maximum ratio is no more than 2/1, but the precise limiting ratio must be determined by routine trial and error testing in a given instance. The amount of carbon monoxide can vary widely, but it is preferred to carry out the reaction under a carbon monoxide pressure of 15 to 3500 psig, preferably 500 to 2500 psig. The amount of catalyst can also vary widely. Most conveniently, the amount of catalyst is between 0.01 and 100 mole percent based on the enol ester, more usually 0.1 to 10 mole percent.

Usually, the reaction is carried out with a solvent. The solvent should be essentially inert under the reaction conditions and should dissolve the reactants and desirably dissolve the active catalyst species, although heterogenous catalysts are possible. Suitable solvents include tetrahydrofuran, benzene, $CH_3CN$, diethyl ether, diethylene glycol dimethyl ether, $CH_2Cl_2$ and $CH_3Cl$. The now preferred solvent is tetrahydrofuran, particularly when using $(\phi_3P)_2PdCl_2$ or $Pd(P\phi_3)_4$ catalyst, or other palladium compounds, although an excess of the hydroxyl compound is also especially useful. Usually, the amount of solvent in the system will be such that the enol ester concentration is at least about 0.01 weight percent in the solution. A special case of a solvent that is not inert, strictly speaking, under the reaction conditions is either of the starting material reactants, i.e., the enol ester or the hydroxy compound. Either can be used in excess of the stoichiometric amount to react with the other reactant. Use of a large excess of water or the organic hydroxyl compound whether or not another solvent, such as THF, is present, helps produce appreciable amounts of the α-hydroxyl acid or ester; thus, the Acyl group is transesterified during the main carboxylation step.

The reaction is normally carried out at a temperature of 0° to 250° C., preferably 20° to 150° C. However, the reaction temperature can be below or above this if desired. As will be understood, optimum reaction temperature varies with the specific reactants. Reaction times on the order of 0.1 to 250 hours can be employed, with reaction times on the order of 2 to 50 hours being more convenient.

Catalysts useful are generally transition metal compounds, particularly coordination complexes of such metals. Palladium coordination complexes are remarkably effective, and especially those complexed with a phosphine, such as P$\phi_3$. Especially useful Pd complexes are ($\phi_3$P)$_2$PdCl$_2$ and (3$\phi_3$P)$_4$Pd with or without a promoter or "co-catalyst" such as HCl or P3.

Other useful catalysts include complexes of Co, Rh, Ni, and other trametals. When Co complexes are used it is advantageous to incorporate hydrogen and a tertiary amine, pyridine or a pyridine derivative into the reaction mixture to enhance catalytic activity.

Once the hydrocarboxylation reaction is completed, the product α-acyloxy acid or ester diastereomers can be recovered from the reaction system in a conventional manner, such as for example, by vacuum distillation or crystallization.

As used herein the term "hydroxyl" in the phrase "organic hydroxyl compound" excludes the hydroxyl group of a carboxylic acid group, —COOH.

The acyloxy acids or esters or the α-hydroxy acids hydrolysis products thereof, are useful in making a chiral column for liquid or gas chromatography by esterifying the solid adsorbent of the column that has pendant OH groups or —COOH groups. Use of the α-hydroxy acids is usually preferred.

The L or D form of the α-hydroxy acids or of the acyloxy acids or esters can be used as a standardizing fluid in an instrument used to measure optical rotation.

The above products can also all be used to prepare specific gravity fluids of different specific gravities, in order to determine the density of solids by the sink or float method.

The following examples are illustrative only and are not to be considered in any way limiting.

EXAMPLE 1

Vinyl L-menthoxyacetate is prepared from acetaldehyde, L-menthoxyacetyl chloride, and pyridine catalyst. A 70 mL stainless steel high pressure reactor fitted with a Pyrex glass liner and magnetic stir bar is charged with THF (5 mL), (PPh$_3$)$_2$PdCl$_2$ (0.05 mmol), CH$_3$OH (0.5 mmol), and vinyl L-menthoxyacetate (0.5 mmol). The reactor is sealed, pressurized to 1000 psig with CO, and stirred for 24 hours at 100° C. The product mixture, isolated after removal of gas from the reactor vessel, contains a diastereomeric mixture of methyl L-menthoxyacetyl-L-lactate and methyl L-menthoxyacetyl-D-lactate. The diastereomers are separated by preparative gas chromatography using an SE-30 liquid phase column. Each diastereomer is hydrolyzed separately by treatment with 2N HCl (aq) for 2 hours at 100° C. to give pure L- and D-lactic acid, methanol, and L-menthoxyacetic acid. The L-menthoxyacetic acid is recycled to L-menthoxyacetyl chloride by treatment with thionyl chloride.

EXAMPLE 2

Vinyl L-menthoxyacetate is prepared from acetaldehyde, L-menthoxyacetic anhydride, and pyridine catalyst. A 70 mL stainless steel high pressure reactor fitted with a Pyrex glass liner and magnetic stir bar is charged with THF (5 mL), (PPh$_3$)$_2$PdCl$_2$ (0.05 mmol), CH$_3$OH (0.5 mmol), and vinyl L-menthoxyacetate (0.5 mmol). The reactor is sealed, pressurized to 1000 psig with CO, and stirred for 24 hours at 100° C. The product mixture, isolated after removal of gas from the reactor vessel, contains a diastereomeric mixture of methyl L-menthoxyacetyl-L-lactate and methyl L-menthoxyacetyl-D-lactate. The diastereomers are separated by preparative gas chromatography using an SE-30 liquid phase column. Each diastereomer is hydrolyzed separately by treatment with 2N HCl (aq) for 2 hours at 100° C. to give pure L- and D-lactic acid, methanol, and L-menthoxyacetic acid. The L-menthoxyacetic acid is recycled to L-menthoxyacetic anhydride by treatment with P$_2$O$_5$.

In each of the following examples, the L-menthoxyacetic acid obtained on hydrolysis of the hydrocarboxylation products is recycled to L-menthoxyacetyl chloride by treatment with thionyl chloride.

EXAMPLE 3

A 70 mL stainless steel high pressure reactor fitted with a Pyrex glass liner and magnetic stir bar is charged with THF (5 mL), (PPh$_3$)$_2$PdCl$_2$ (0.05 mmol), ethanol (0.5 mmol), and vinyl L-menthoxyacetate (0.5 mmol). The reactor is sealed, pressurized to 1000 psig with CO, and stirred for 24 hours at 100° C. The product mixture, isolated after removal of gas from the reactor vessel, contains a diastereomeric mixture of ethyl L-menthoxyacetyl-L-lactate and ethyl L-menthoxyacetyl-D-lactate. The diastereomers are separated by preparative gas chromatography using an SE-30 liquid phase column. Each diastereomer is hydrolyzed separately by treatment with 2N HCl (aq) for 2 hours at 100° C. to give pure L- and D-lactic acid, ethanol, and L-menthoxyacetic acid.

EXAMPLE 4

A 70 mL stainless steel high pressure reactor fitted with a Pyrex glass liner and magnetic stir bar is charged with THF (5 mL), (PPh$_3$)$_2$PdCl$_2$ (0.05 mmol), 2-propanol (0.5 mmol), and vinyl L-menthoxyacetate (0.5 mmol). The reactor is sealed, pressurized to 1000 psig with CO, and stirred for 24 hours at 100° C. The product mixture, isolated after removal of gas from the reactor vessel, contains a diastereomeric mixture of 2-propyl L-menthoxyacetyl-L-lactate and 2-propyl L-menthoxyacetyl-D-lactate. The diastereomers are separated by preparative gas chromatography using an SE-30 liquid phase column. Each diastereomer is hydrolyzed separately by treatment with 2N HCl (aq) for 2 hours at 100° C. to give pure L- and D-lactic acid, 2-propanol, and L-menthoxyacetic acid. The L-menthoxyacetic acid is recycled to L-menthoxyacetyl chloride by treatment with thionyl chloride.

EXAMPLE 5

A 70 mL stainless steel high pressure reactor fitted with a Pyrex glass liner and magnetic stir bar is charged with THF (5 mL), (PPh$_3$)$_2$PdCl$_2$ (0.05 mmol), tert-butanol (0.5 mmol), and vinyl L-menthoxyacetate (0.5 mmol). The reactor is sealed, pressurized to 1000 psig with CO, and stirred for 24 hours at 100° C. The product mixture, isolated after removal of gas from the reactor vessel, contains a diastereomeric mixture of tert-butyl L-menthoxyacetyl-L-lactate and tert-butyl L-menthoxyacetyl-D-lactate. The diastereomers are separated by preparative gas chromatography using an SE-30 liquid phase column. Each diastereomer is hydrolyzed separately by treatment with 2N HCl (aq) for 2 hours at 100° C. to give pure L- and D-lactic acid, tert-butanol, and L-menthoxyacetic acid.

EXAMPLE 6

A 70 mL stainless steel high pressure reactor fitted with a Pyrex glass liner and magnetic stir bar is charged with THF (5 mL), $(PPh_3)_2PdCl_2$ (0.05 mmol), n-butanol (0.5 mmol), and vinyl L-menthoxyacetate (0.5 mmol). The reactor is sealed, pressurized to 1000 psig with CO, and stirred for 24 hours at 100° C. The product mixture, isolated after removal of gas from the reactor vessel, contains a diastereomeric mixture of n-butyl L-menthoxyacetyl-L-lactate and n-butyl L-menthoxyacetyl-D-lactate. The diastereomers are separated by preparative gas chromatography using an SE-30 liquid phase column. Each diastereomer is hydrolyzed separately by treatment with 2N HCl (aq) for 2 hours at 100° C. to give pure L- and D-lactic acid, n-butanol, and L-menthoxyacetic acid.

EXAMPLE 7

A 70 mL stainless steel high pressure reactor fitted with a Pyrex glass liner and magnetic stir bar is charged with THF (5 mL), $(PPh_3)_2PdCl_2$ (0.05 mmol), water (0.5 mmol), and vinyl L-menthoxyacetate (0.5 mmol). The reactor is sealed, pressurized to 1000 psig with CO, and stirred for 24 hours at 100° C. The product mixture, isolated after removal of gas from the reactor vessel, contains a diastereomeric mixture of L-menthoxyacetyl-L-lactic acid and L-menthoxyacetyl-D-lactic acid. The diastereomers are separated by fractional crystallization. Each diastereomer is hydrolyzed separately by treatment with 2N HCl (aq) for 2 hours at 100° C. to give pure L-and D-lactic acid and L-menthoxyacetic acid.

EXAMPLE 8

A 70 mL stainless steel high pressure reactor fitted with a Pyrex glass liner and magnetic stir bar is charged with THF (5 mL), $(PPh_3)_4Pd$ (0.05 mmol), HCl (0.10 mmol), $CH_3OH$ (0.5 mmol), and vinyl L-menthoxyacetate (0.5 mmol). The reactor is sealed, pressurized to 1000 psig with CO, and stirred for 24 hours at 100° C. The product mixture, isolated after removal of gas from the reactor vessel, contains a diastereomeric mixture of methyl L-menthoxyacetyl-L-lactate and methyl L-menthoxyacetyl-D-lactate. The diastereomers are separated by preparative gas chromatography using an SE-30 liquid phase column. Each diastereomer is hydrolyzed separately by treatment with 2N HCl (aq) for 2 hours at 100° C. to give pure L- and D-lactic acid, methanol, and L-menthoxyacetic acid.

EXAMPLE 9

A 70 mL stainless steel high pressure reactor fitted with a Pyrex glass liner and magnetic stir bar is charged with THF (5 mL), $RhCl_3.H_2O$ (0.05 mmol), HI (0.10 mmol), $CH_3OH$ (0.5 mmol), and vinyl L-menthoxyacetate (0.5 mmol). The reactor is sealed, pressurized to 1000 psig with CO, and stirred for 24 hours at 100° C. The product mixture, isolated after removal of gas from the reactor vessel, contains a diastereomeric mixture of methyl L-menthoxyacetyl-L-lactate and methyl L-menthoxyacetyl-D-lactate. The diastereomers are separated by preparative gas chromatography using an SE-30 liquid phase column. Each diastereomer is hydrolyzed separately by treatment with 2N HCl (aq) for 2 hours at 100° C. to give pure L- and D-lactic acid, methanol, and L-menthoxyacetic acid.

EXAMPLE 10

A 70 mL stainless steel high pressure reactor fitted with a Pyrex glass liner and magnetic stir bar is charged with THF (5 mL), $NiI_2.6H_2O$ (0.05 mmol), $CH_3OH$ (0.5 mmol), and vinyl L-menthoxyacetate (0.5 mmol). The reactor is sealed, pressurized to 1000 psig with CO, and stirred for 24 hours at 100° C. The product mixture, isolated after removal of gas from the reactor vessel, contains a diastereomeric mixture of methyl L-menthoxyacetyl-L-lactate and methyl L-menthoxyacetyl-D-lactate. The diastereomers are separated by preparative gas chromatography using an SE-30 liquid phase column. Each diastereomer is hydrolyzed separately by treatment with 2N HCl (aq) for 2 hours at 100° C. to give pure L- and D-lactic acid, methanol, and L-menthoxyacetic acid.

EXAMPLE 11

A 70 mL stainless steel high pressure reactor fitted with a Pyrex glass liner and magnetic stir bar is charged with THF (5 mL), $(Ph_2P)_2Ni(CO)_2$ (0.05 mmol), $CH_3OH$ (0.5 mmol), and vinyl L-menthoxyacetate (0.5 mmol). The reactor is sealed, pressurized to 1000 psig with CO, and stirred for 24 hours at 100° C. The product mixture, isolated after removal of gas from the reactor vessel, contains a diastereomeric mixture of methyl L-menthoxyacetyl-L-lactate and methyl L-menthoxyacetyl-D-lactate. The diastereomers are separated by preparative gas chromatography using an SE-30 liquid phase column. Each diastereomer is hydrolyzed separately by treatment with 2N HCl (aq) for 2 hours at 100° C. to give pure L- and D-lactic acid, methanol, and L-menthoxyacetic acid.

EXAMPLE 12

A 70 mL stainless steel high pressure reactor fitted with a Pyrex glass liner and magnetic stir bar is charged with THF (5 mL), $[Rh(CO)_2Cl]_2$ (0.05 mmol), $CH_3OH$ (0.5 mmol), and vinyl L-menthoxyacetate (0.5 mmol). The reactor is sealed, pressurized to 1000 psig with CO, and stirred for 24 hours at 100° C. The product mixture, isolated after removal of gas from the reactor vessel, contains a diastereomeric mixture of methyl L-menthoxyacetyl-L-lactate and methyl L-menthoxyacetyl-D-lactate. The diastereomers are separated by preparative gas chromatography using an SE-30 liquid phase column. Each diastereomer is hydrolyzed separately by treatment with 2N HCl (aq) for 2 hours at 100° C. to give pure L- and D-lactic acid, methanol, and L-menthoxyacetic acid.

EXAMPLE 13

A 70 mL stainless steel high pressure reactor fitted with a Pyrex glass liner and magnetic stir bar is charged with THF (5 mL), palladium acetate (0.05 mmol), $CH_3OH$ (0.5 mmol), and vinyl L-menthoxyacetate (0.5 mmol). The reactor is sealed, pressurized to 1000 psig with CO, and stirred for 24 hours at 100° C. The product mixture, isolated after removal of gas from the reactor vessel, contains a diastereomeric mixture of methyl L-menthoxyacetyl-L-lactate and methyl L-menthoxyacetyl-D-lactate. The diastereomers are separated by preparative gas chromatography using an SE-30 liquid phase column. Each diastereomer is hydrolyzed separately by treatment with 2N HCl (aq) for 2 hours at 100° C. to give pure L- and D-lactic acid, methanol, and L-menthoxyacetic acid.

EXAMPLE 14

A 70 mL stainless steel high pressure reactor fitted with a Pyrex glass liner and magnetic stir bar is charged with THF (5 mL), $Co_2(CO)_8$ (0.05 mmol), pyridine (0.50 mmol), $CH_3OH$ (0.5 mmol), and vinyl L-menthoxyacetate (0.5 mmol). The reactor is sealed, pressurized to 1500 psig with 3:1 $CO:H_2$, and stirred for 24 hours at 100° C. The product mixture, isolated after removal of gas from the reactor vessel, contains a diastereomeric mixture of methyl L-menthoxyacetyl-L-lactate and methyl L-menthoxyacetyl-D-lactate. The diastereomers are separated by preparative gas chromatography using an SE-30 liquid phase column. Each diastereomer is hydrolyzed separately by treatment with 2N HCl (aq) for 2 hours at 100° C. to give pure L- and D-lactic acid, methanol, and L-menthoxyacetic acid.

EXAMPLE 15

1-Propenyl L-menthoxyacetate is prepared from propionaldehyde, L-menthoxyacetyl chloride, and pyridine catalyst. A 70 mL stainless steel high pressure reactor fitted with a Pyrex glass liner and magnetic stir bar is charged with THF (5 mL), $PPh_3)_2PdCl_2$ (0.05 mmol), $CH_3OH$ (0.5 mmol), and 1-propenyl L-menthoxyacetate (0.5 mmol). The reactor is sealed, pressurized to 1000 psig with CO, and stirred for 24 hours at 100° C. The product mixture, isolated after removal of gas from the reactor vessel, contains a diastereomeric mixture of methyl L-menthoxyacetyl-L-2-hydroxybutyrate and methyl L-menthoxyacetyl-D-2-hydroxybutyrate. The diastereomers are separated by preparative gas chromatography using an SE-30 liquid phase column. Each diastereomer is hydrolyzed separately by treatment with 2N HCl (aq) for 2 hours at 100° C. to give pure L- and D-2-hydroxybutyric acid, methanol, and L-menthoxyacetic acid.

EXAMPLE 16

2-L-menthoxyacetyloxy-2-butene is prepared from 2-butanone, L-menthoxyacetyl chloride, and pyridine catalyst. A 70 mL stainless steel high pressure reactor fitted with a Pyrex glass liner and magnetic stir bar is charged with THF (5 mL), $(PPh_3)_2PdCl_2$ (0.05 mmol), $CH_3OH$ (0.5 mmol), and 2-L-menthoxyacetyloxy-2-butene (0.5 mmol). The reactor is sealed, pressurized to 1000 psig with CO, and stirred for 24 hours at 100° C. The product mixture, isolated after removal of gas from the reactor vessel, contains a diastereomeric mixture of methyl 2-L-menthoxyacetyloxy-L-2-methylbutyrate and methyl 2-L-menthoxyacetyl-D-2-methylbutyrate. The diastereomers are separated by preparative gas chromatography using an SE-30 liquid phase column. Each diastereomer is hydrolyzed separately by treatment with 2N HCl (aq) for 2 hours at 100° C. to give pure L- and D-2-methyl-2-hydroxybutyric acid, methanol, and L-menthoxyacetic acid.

EXAMPLE 17

1-L-menthoxyacetyloxy-2-methylpropene is prepared from isobutyraldehyde, L-menthoxyacetyl chloride, and pyridine catalyst. A 70 mL stainless steel high pressure reactor fitted with a Pyrex glass liner and magnetic stir bar is charged with THF (5 mL), $(PPh_3)_2PdCl_2$ (0.05 mmol), $CH_3OH$ (0.5 mmol), and 1-L-menthoxyacetyloxy-2-methylpropene (0.5 mmol). The reactor is sealed, pressurized to 1000 psig with CO, and stirred for 24 hours at 100° C. The product mixture, isolated after removal of gas from the reactor vessel, contains a diastereomeric mixture of methyl 2-L-menthoxyacetyloxy-L-3-methylbutyrate and methyl 2-L-menthoxyacetyl-D-3-methylbutyrate. The diastereomers are separated by preparative gas chromatography using an SE-30 liquid phase column. Each diastereomer is hydrolyzed separately by treatment with 2N HCl (aq) for 2 hours at 100° C. to give pure L- and D-2-hydroxy-3-methylbutyric acid, methanol, and L-menthoxyacetic acid.

EXAMPLE 18

2-L-menthoxyacetyloxy-3-methyl-2-butene is prepared from 3-methyl-2-butanone, L-methoxyacetyl chloride, and pyridine catalyst. A 70 mL stainless steel high pressure reactor fitted with a Pyrex glass liner and magnetic stir bar is charged with THF (5 mL), $(PPh_3)_2PdCl_2$ (0.5 mmol), $CH_3OH$ (0.5 mmol), and 2-L-menthoxyacetyloxy-3-methyl-2-butene (0.5 mmol). The reactor is sealed, pressurized to 1000 psig with CO, and stirred for 24 hours at 100° C. The product mixture, isolated after removal of gas from the reactor vessel, contains a diastereomeric mixture of methyl 2-L-menthoxyacetyl-2,3-dimethyl-L-2-hydroxybutyrate and methyl 2-L-menthoxyacetyl-2,3-dimethyl-D-2-hydroxybutyrate. The diastereomers are separated by preparative gas chromatography using an SE-30 liquid phase column. Each diastereomer is hydrolyzed separately by treatment with 2N HCl (aq) for 2 hours at 100° C. to give pure L- and D-2,3-dimethyl-2-hydroxybutyric acid, methanol, and L-menthoxyacetic acid.

EXAMPLE 19

1-L-methoxyacetyloxy-3-methylthiopropene is prepared from 3-methylthiopropionaldehyde, L-menthoxyacetyl chloride, and pyridine catalyst. A 70 mL stainless steel high pressure reactor fitted with a Pyrex glass liner and magnetic stir bar is charged with THF (5 mL), $(PPh_3)_2PdCl_2$ (0.05 mmol), $CH_3OH$ (0.5 mmol), and 1-L-menthoxyacetyloxy-3-methylthiopropene (0.5 mmol). The reactor is sealed, pressurized to 1000 psig with CO, and stirred for 24 hours at 100° C. The product mixture, isolated after removal of gas from the reactor vessel, contains a diastereomeric mixture of methyl 2-L-menthoxyacetyl-4-methylthio-L-2-hydroxybutyrate and methyl 2-L-menthoxyacetyl-4-methylthio-D-2-hydroxybutyrate. The diastereomers are separated by preparative gas chromatography using an SE-30 liquid phase column. Each diastereomer is hydrolyzed separately by treatment with 2N HCl (aq) for 2 hours at 100° C. to give pure L- and D-4-methylthio-2-hydroxybutyric acid (methionine hydroxy analog), methanol, and L-menthoxyacetic acid.

EXAMPLE 20

R-3-methylpentanal is prepared by treatment of acetaldehyde with 1 equivalent of n-butyllithium and treating the resulting enolate with 1 equivalent of S-2-butyl tosylate. R-1-acetyloxy-3-methyl-1-pentene is then prepared from R-3-methylpentanal, acetyl chloride, and pyridine catalyst. A 70 mL stainless steel high pressure reactor fitted with a pyrex glass liner is charged with THF (5 mL), $(PPh_3)_2PdCl_2$ (0.05 mmol), $CH_3OH$ (0.5 mmol), and R-1-acetyloxy-3-methyl-1-pentene (0.5 mmol). The reactor is sealed, pressurized to 1000 psig with CO, and stirred for 24 hours at 100° C. The product mixture, isolated after removal of gas from the reaction vessel, contains a diastereomeric mixture of RR-2-acetyloxy-4-methylhexanoic acid methyl ester and SR-2-acetyloxy-4-methylhexanoic acid methyl ester. The diastereomeric mixture is hydrolyzed by treatment with 2N $HCl_{(aq)}$ for 2 hours at 100° C. to give a diastereomeric mixture of RR-2-acetyloxy-4-methylhexanoic acid and SR-2-acetyloxy-4-methylhexanoic acid. The diastereomers are then separated by preparative gas chromatography using an SE-30 liquid phase column.

As will be evident to those skilled in the art, various modifications of this invention can be made or followed in the light of foregoing disclosure and discussion without departing from the spirit and scope of the disclosure or from the scope of the claims.

We claim:

1. A process for making an α-hydroxy acid which is essentially all L or all D with respect to the chiral C atom bonded to the carboxy group of said acid which comprises (1) hydrocarboxylating an enol acylate, which has a chiral C atom that is essentially all L or all D, with CO and water or an organic hydroxyl compound, thereby producing a reaction mixture containing diastereomeric α-acyloxy acids or esters having two chiral centers and having essentially no enantiomeric pairs, (2) separating the diastereomers by conventional physical means and (3) hydrolyzing at least one of said separated diastereomers to make at least the α-hydroxy acid which is essentially all L or all D with respect to the chiral C atom bonded to the carboxy group of said acid, said hydrocarboxylating step simultaneously creating (a) said α-acyloxy acid or ester (b) the chirality of the alpha C atom in L, D form and (c) the second chiral center in said α-acyloxy acid or ester in essentially all L or all D form.

2. A process for making an α-hydroxy acid which is essentially all L or all D with respect to the chiral C atom bonded to the carboxy group of said acid which comprises (1) hydrocarboxylating an enol acylate, which has a chiral C atom that is essentially all L or all D, with CO and an organic hydroxyl compound, esters having two chiral centers and having essentially no enantiomeric pairs, (2) separating the diastereomers by conventional physical means and (3) hydrolyzing at least one of said separated diastereomers to make at least the α-hydroxy acid which is essentially all L or all D with respect to the chiral C atom bonded to the carboxy group of said acid, said hydrocarboxylating step simultaneously creating (a) said α-acyloxy ester (b) the chirality of the alpha C atom in L, D form and (c) the second chiral center in said α-acyloxy ester in essentially all L or all D form.

3. A process for making an α-hydroxy acid which is essentially all L or all D with respect to the chiral C atom bonded to the carboxy group of said acid which comprises (1) hydrocarboxylating an enol acylate, the enol portion of which has a chiral C atom that is essentially all L or all D, with CO and water or an organic hydroxyl compound, thereby producing a reaction mixture containing diastereomeric α-acyloxy acids or esters having two chiral centers and having essentially no enantiomeric pairs, (2) hydrolyzing the product of (1) to make a diastereomeric mixture containing α-hydroxy acids, and (3) separating by conventional physical means from the product of (2) at least one α-hydroxy acid which is essentially all L or all D with respect to the chiral C atom bonded to the carboxy group of said acid, said hydrocarboxylating step simultaneously creating (a) said α-acyloxy acid or ester (b) the chirality of the alpha C atom in L, D form and (c) the second chiral center in said α-acyloxy acid or ester in essentially all L or all D form.

4. A process for making an α-hydroxy acid which is essentially all L or all D with respect to the chiral C atom bonded to the carboxy group of said acid which comprises (1) hydrocarboxylating an enol acylate, the enol portion of which has a chiral C atom that is essentially all L or all D, with CO and an organic hydroxyl compound, thereby producing a reaction mixture containing diastereomeric α-acyloxy esters having two chiral centers and having essentially no enantiomeric pairs, (2) hydrolyzing the product of (1) to make a diastereomeric mixture containing α-hydroxy acids, and (3) separating by conventional physical means from the product of (2) at least one α-hydroxy acid which is essentially all L or all D with respect to the chiral C atom bonded to the carboxy group of said acid, said hydrocarboxylating step simultaneously creating (a) said α-acyloxy ester (b) the chirality of the alpha C atom in L, D form and (c) the second chiral center in said α-acyloxy ester in essentially all L or all D form.

5. The process comprising the steps of (1) hydrocarboxylating an enol acylate with CO and water or an organic hydroxyl compound to product an α-acyloxy acid or ester, using as the enol acylate reactant, an enol acylate, the enol portion of which has a chiral center that is essentially all L or all D, thereby producing a reaction mixture containing diastereomeric α-acyloxy acids or esters having two chiral centers and having essentially no enantiomeric pairs and (2) hydrolyzing the product of (1) to make a diastereomeric mixture containing α-hydroxy acids which are easily separable by conventional physical means, said hydrocarboxylating step simultaneously creating (a) said α-acyloxy acid or ester (b) the chirality of the alpha C atom in L, D form and (c) the second chiral center in said α-acyloxy acid or ester in essentially all L or all D form.

6. The process comprising the steps of (1) hydrocarboxylating an enol acylate with CO and an organic hydroxyl compound to product an α-acyloxy ester, using as the enol acylate reactant, an enol acylate, the enol portion of which has a chiral center that is essentially all L or all D, thereby producing a reaction mixture containing diastereomeric α-acyloxy esters having two chiral centers and having essentially no enantiomeric pairs and (2) hydrolyzing the product of (1) to make a diastereomeric mixture containing α-hydroxy acids which are easily separable to conventional physical means, said hydrocarboxylating step simultaneously creating (a) said α-acyloxy acid or ester (b) the chirality of the alpha C atom in L, D form and (c) the second chiral center in said α-acyloxy acid or ester in essentially all L or all D form.

7. The process comprising the steps of (1) hydrocarboxylating an enol acylate with CO and water or an organic hydroxyl compound to produce an α-acyloxy acid or ester, using as the enol acylate reactant, an enol acylate, the enol portion of which has a chiral center that is essentially all L or all D, thereby producing a reaction mixture containing diastereomeric α-acyloxy acids or esters having two chiral centers and having essentially no enantiomeric pairs, (2) separating the diastereomers by conventional physical means, (3) hydrolyzing at least one of said separated diastereomers to make at least the α-hydroxy acid which is essentially all L or all D with respect to the chiral C atom bonded to the carboxy group of said acid, said hydrocarboxylating step simultaneously creating (a) said α-acyloxy acid or ester (b) the chirality of the alpha C atom in L, D form and (c) the second chiral center in said α-acyloxy acid or ester in essentially all L or all D form.

8. The process comprising the steps of (1) hydrocarboxylating an enol acylate with CO and water or an organic hydroxyl compound to produce an α-acyloxy acid or ester, using as the enol acylate reactant, an enol acylate, the enol portion of which has a chiral center that is essentially all L or all D, thereby producing a reaction mixture containing diastereomeric α-acyloxy acids or esters having two chiral centers and having essentially no enantiomeric pairs, (2) hydrolyzing the product of (1) to make a diastereomeric mixture containing α-hydroxy acids and (3) separating at least a portion of the L- or of the D-α-hydroxy acid from said mixture by conventional physical means, said hydrocarboxylating step simultaneously creating (a) said α-acyloxy acid or ester (b) the chirality of the alpha C atom in L, D form and (c) the second chiral center in said α-acyloxy acid or ester in essentially all L or all D form.

* * * * *